(12) United States Patent
Hayashi et al.

(10) Patent No.: US 9,366,663 B2
(45) Date of Patent: Jun. 14, 2016

(54) SAMPLE CARTRIDGE AND DEVICE FOR MEASURING ELECTRICAL CHARACTERISTICS OF LIQUID SAMPLE

(75) Inventors: Yoshihito Hayashi, Chiba (JP); Yoichi Katsumoto, Tokyo (JP)

(73) Assignee: SONY CORPORATION, Tokyo (JP)

( * ) Notice: Subject to any disclaimer, the term of this patent is extended or adjusted under 35 U.S.C. 154(b) by 293 days.

(21) Appl. No.: 13/217,918

(22) Filed: Aug. 25, 2011

(65) Prior Publication Data

US 2012/0048732 A1 Mar. 1, 2012

(30) Foreign Application Priority Data

Sep. 1, 2010 (JP) ................ P2010-195533

(51) Int. Cl.
*G01N 27/07* (2006.01)
*G01N 27/403* (2006.01)
*G01N 33/49* (2006.01)
*G01N 33/86* (2006.01)
*G01N 27/02* (2006.01)

(52) U.S. Cl.
CPC ............ *G01N 33/4905* (2013.01); *G01N 33/86* (2013.01); *G01N 27/026* (2013.01)

(58) Field of Classification Search
CPC .. G01N 33/4905; G01N 33/86; G01N 27/026
See application file for complete search history.

(56) References Cited

U.S. PATENT DOCUMENTS

| 5,068,617 | A | 11/1991 | Reich | |
|---|---|---|---|---|
| 2002/0049557 | A1* | 4/2002 | Chen | 702/116 |
| 2004/0072357 | A1* | 4/2004 | Stiene et al. | 436/69 |
| 2008/0221805 | A1* | 9/2008 | Andrews | 702/19 |
| 2009/0201035 | A1* | 8/2009 | Kaltenbach et al. | 324/695 |
| 2010/0136606 | A1 | 6/2010 | Katsumoto et al. | |
| 2011/0079521 | A1* | 4/2011 | Revol-Cavalier | 205/789 |

FOREIGN PATENT DOCUMENTS

| CN | 100582766 | 1/2010 |
|---|---|---|
| JP | 02-132362 | 5/1990 |
| JP | 2009-042141 | 2/2009 |
| JP | 2010-181400 | 8/2010 |
| WO | 2010079845 | 7/2010 |

OTHER PUBLICATIONS

Japanese Patent Office, Office Action issued in connection with Japanese Patent Application No. 2010-195533, dated Jan. 28, 2014. (3 pages).

Notification of the First Office Action issued in connection with Chinese Patent Application No. 2011102563356, dated Oct. 21, 2014. (20 pages).

* cited by examiner

*Primary Examiner* — Lyle Alexander
*Assistant Examiner* — Robert Eom
(74) *Attorney, Agent, or Firm* — Chip Law Group

(57) ABSTRACT

A sample cartridge for measuring the electrical characteristics of a liquid sample, which is made by forming an insulating material into a tubular body and is capable of holding the liquid sample in a region that is constituted by the surfaces of electrodes that are respectively inserted from openings of both ends into an inner cavity and the surface of the inner cavity, and in which a narrowing portion located between two facing electrodes and having a narrowed inner cavity is provided in the region.

10 Claims, 5 Drawing Sheets

SAMPLE CARTRIDGE AND DEVICE FOR MEASURING ELECTRICAL CHARACTERISTICS OF LIQUID SAMPLE

CROSS REFERENCES TO RELATED APPLICATIONS

The present application claims priority to Japanese Priority Patent Application JP 2010-195533 filed in the Japan Patent Office on Sep. 1, 2010, the entire contents of which are hereby incorporated by reference.

BACKGROUND

The present application relates to a sample cartridge and a device for measuring the electrical characteristics of a liquid sample. More specifically, the present disclosure relates to a sample cartridge or the like, which has a structure for measuring the electrical characteristics of a liquid sample with a high precision.

Measuring the electrical characteristics of a liquid sample and then determining the physical properties of the sample from the measurement result or discriminating the kind of a cell or the like that is included in the sample are performed (refer to Japanese Unexamined Patent Application Publication No. 2009-042141, for example). As the electrical characteristics that are measured, complex permittivity or its frequency dispersion (dielectric spectrum) can be given. The complex permittivity or its frequency dispersion is generally calculated by measuring complex capacitance or complex impedance between electrodes by using a solution retainer or the like provided with electrodes for applying voltage to a solution.

In Japanese Unexamined Patent Application Publication No. 2010-181400, a technique of acquiring the information about blood coagulation from the permittivity of blood is disclosed and "a blood coagulation system analysis device including a pair of electrodes, an applying means for applying alternating voltage to the pair of electrodes at predetermined time intervals, a measuring means for measuring the permittivity of blood disposed between the pair of electrodes, and an analysis means for analyzing the degree of working of a blood coagulation system by using the permittivity of the blood which is measured at the predetermined time intervals since an anticoagulant action acting on the blood has been released" is described.

In the past, as a test of a blood coagulation system, a prothrombin time or an activated partial thromboplastin time has been widely known. In the blood coagulation system analysis device described in Japanese Unexamined Patent Application Publication No. 2010-181400, it is possible to analyze the working of an early blood coagulation system by using a temporal change of permittivity before a time when blood begins to coagulate from the dynamic viewpoint of viscoelasticity. For this reason, it is considered that compared to a test method in the past, it is possible to increase an analysis precision and it is possible to perform early analysis.

SUMMARY

In the measurement of the electrical characteristics of a liquid sample, contact between the liquid sample and electrodes for applying an electric field to a sample solution is inevitable. However, there is a case where a chemical reaction of the liquid sample progresses in the contact surface with the electrode. In this case, the chemical reaction affects a measurement result, so that it does not become possible to accurately measure the electrical characteristics of the liquid sample. For example, in a case where blood is filled up between parallel-plate type capacitor-like electrodes and a coagulation process thereof is then measured, an intrinsic coagulation reaction of the blood is activated due to the contact with the electrode surface, so that a coagulation process is accelerated further than the original one, whereby there is a case where it is not possible to obtain a correct measurement result.

Further, in the measurement of the electrical characteristics of a liquid sample, there is a case where interfacial polarization occurs at the contact surface between the liquid sample and the electrode, and also in this case, it becomes difficult to accurately measure the electrical characteristics of the liquid sample due to the influence of the interfacial polarization.

It is desirable to provide a technique for measuring the electrical characteristics of a liquid sample with a high precision by suppressing the influence of a chemical reaction or interfacial polarization of the liquid sample in the contact surface with an electrode on a measurement result.

According to an embodiment, there is provided a sample cartridge for measuring the electrical characteristics of a liquid sample, which is made by forming an insulating material into a tubular body and is capable of holding the liquid sample in a region that is constituted by the surfaces of electrodes that face each other and are respectively inserted from openings of both ends into an inner cavity and the surface of the inner cavity, and in which a narrowing portion located between the two facing electrodes and having a narrowed inner cavity is provided in the region.

In the sample cartridge of the embodiment, the cross-sectional area of the inner cavity of the narrowing portion may be smaller than the area of each electrode surface constituting the region.

According to this configuration, in the sample cartridge, the complex impedance of the liquid sample filled up in the entirety of the region becomes approximately equal to the complex impedance of the liquid sample present in a narrowing region.

The sample cartridge may have the electrodes as an internal configuration.

Further, according to another embodiment, there is provided a device for measuring the electrical characteristics of a liquid sample, including: a pair of electrodes for applying voltage to the liquid sample; a sample cartridge which is made by forming an insulating material into a tubular body and is capable of holding the liquid sample in a region that is constituted by the surfaces of the electrodes that face each other and are respectively inserted from openings of both ends into an inner cavity and the surface of the inner cavity, and in which a narrowing portion located between the two facing electrodes and having a narrowed inner cavity is provided in the region; an applying section which applies voltage to the electrodes; and a measuring section which measures the electrical characteristics of the liquid sample.

In the electrical characteristic measuring device, the complex impedance of the liquid sample filled up in the entirety of the region becomes approximately equal to the complex impedance of the liquid sample present in a narrowing region.

The electrical characteristic measuring device can be preferably applied as a blood coagulation system analysis device by using blood as the liquid sample and measuring the permittivity of the blood.

According to the present application, a technique for measuring the electrical characteristics of a liquid sample with a high precision by suppressing the influence of a chemical reaction or interfacial polarization of the liquid sample in the contact surface with an electrode on a measurement result is provided.

Additional features and advantages are described herein, and will be apparent from the following Detailed Description and the figures.

DETAILED DESCRIPTION

Embodiments of the present application will be described below in detail with reference to the drawings.

In addition, an embodiment which will be described below is to illustrate one example of a typical embodiment and the scope is not to be narrowly construed by the embodiment. In addition, a description will be made in the following order.

Figure 1:
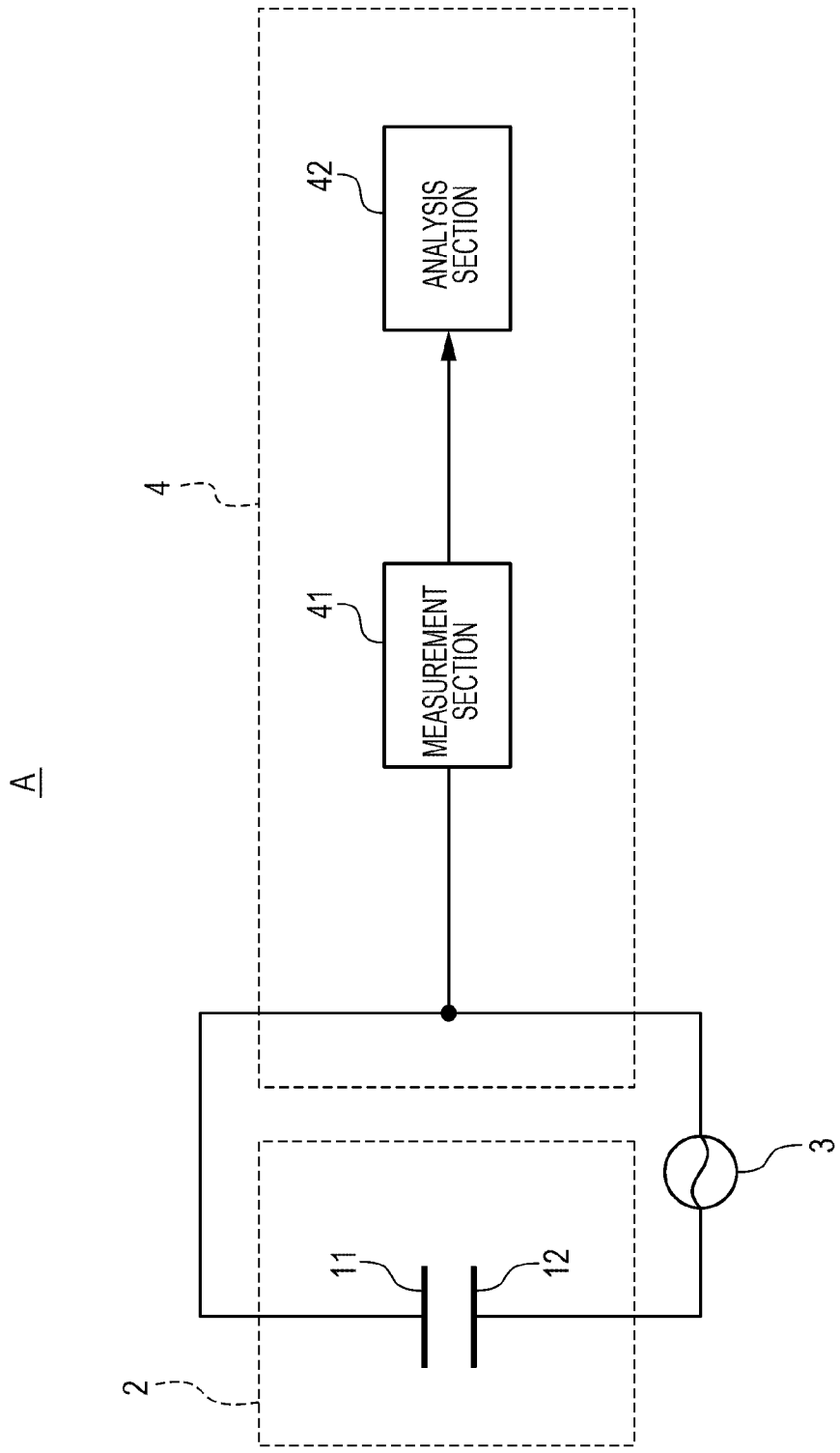
FIG. 1 is a schematic diagram for illustrating a schematic configuration of an electrical characteristic measuring device related to the present application.

1. Electrical Characteristic Measuring Device of Liquid Sample
  (1) Overall Configuration of Device
  (2) Configuration of Sample Cartridge
1. Electrical Characteristic Measuring Device of Liquid Sample
  (1) Overall Configuration of Device In FIG. 1, a schematic configuration of an electrical characteristic measuring device (hereinafter also simply referred to as a "measuring device") of a liquid sample related to the present application is illustrated.

In the drawing, a measuring device denoted by a symbol A includes a sample cartridge 2 which holds a liquid sample, a pair of electrodes 11 and 12 which apply voltage to the liquid sample held in the sample cartridge 2, an electric power supply (applying section) 3 which applies voltage to the electrodes 11 and 12, and a measurement section (measuring section) 41 which measures the electrical characteristics of the liquid sample. The measurement section 41 constitutes a signal processing section 4 along with an analysis section 42 which receives the output of a measurement result from the measurement section 41 and performs physical properties determination or the like on the liquid sample.

At the sample cartridge 2 and/or the signal processing section 4, a temperature sensor (not shown) and a thermoelectric element (not shown) are provided. The measuring device A measures the temperature of the liquid sample by using the temperature sensor and provides the amount of a signal corresponding to the measured result to the thermoelectric element, thereby adjusting the temperature of the liquid sample.

The electric power supply 3 applies voltage at the point of time of receiving a measurement starting command or the point of time of power-on as a starting point of time. Specifically, the electric power supply 3 applies alternating-current voltage of a predetermined frequency to the electrodes 11 and 12 for each measurement interval which is set. In addition, the voltage that the electric power supply 3 applies may be set to be direct-current voltage in accordance with electrical characteristics that are measured.

The measurement section 41 measures electrical characteristics such as complex permittivity (hereinafter also simply referred to as "permittivity") or its frequency dispersion at the point of time of receiving a measurement starting command or the point of time of power-on as a starting point of time. Specifically, for example, in a case where permittivity is measured, the measurement section 41 measures an electric current or impedance between the electrodes 11 and 12 in a predetermined period and derives permittivity from the measurement value. In the derivation of permittivity, an existing function or relational expression which expresses the relationship between an electric current or impedance and permittivity is used.

Data (hereinafter also referred to as "permittivity data") expressing the permittivity derived from the measurement section 41 is provided to the analysis section 42 for each measurement interval. The analysis section 42 receives the permittivity data which is provided from the measurement section 41 and then starts physical properties determination or the like on the liquid sample. The analysis section 42 gives notice of one or both of the result of the physical properties determination or the like of the liquid sample and the permittivity data. This notice is performed, for example, by graphic display on a monitor or printing on a given medium.

In Japanese Unexamined Patent Application Publication No. 2010-181400 mentioned above, the inventors clarify that a temporal change in permittivity of blood reflects a coagulation process of blood and an ascending change in permittivity can become an index which quantitatively expresses the degree of hypercoaguability or coagulation ability of blood. Especially, according to the measurement of permittivity, it is possible to observe a blood coagulation process of an initial stage, the observation of which is not possible in a free damped oscillation type rheometer in the past.

Accordingly, if in the measuring device A, blood is used as the liquid sample, it is possible to perform analysis of a blood coagulation system from the permittivity data of blood. Specifically, for example, in the analysis section 42, a straight line which most approximates permittivities that a plurality of permittivity data items received within an analysis period respectively represents is detected. Then, a gradient of the detected straight line is sought as a parameter which represents the amount of increase in permittivity of an initial stage of a blood coagulation process, and the degree of hypercoaguability or coagulation ability of blood is predicted from the gradient. Since the larger the gradient of the straight line, the larger the degree of hypercoaguability or coagulation ability of blood, the prediction is performed, for example, on the basis of a database or a function, in which the degree and the gradient of the straight line are correlated with each other. By predicting the degree of hypercoaguability or coagulation ability of blood on the basis of the gradient of the detected straight line in this manner, it becomes possible to perform the analysis of a blood coagulation system in a short period of time.

The configuration of the measuring device A described above can be a device equivalent to or with appropriate modifications applied to that of a blood coagulation system analysis device that the inventors disclose in Japanese Unexamined Patent Application Publication No. 2010-181400, except for the configuration of the sample cartridge 2 which will be next described.

(2) Configuration of Sample Cartridge

Figure 2:
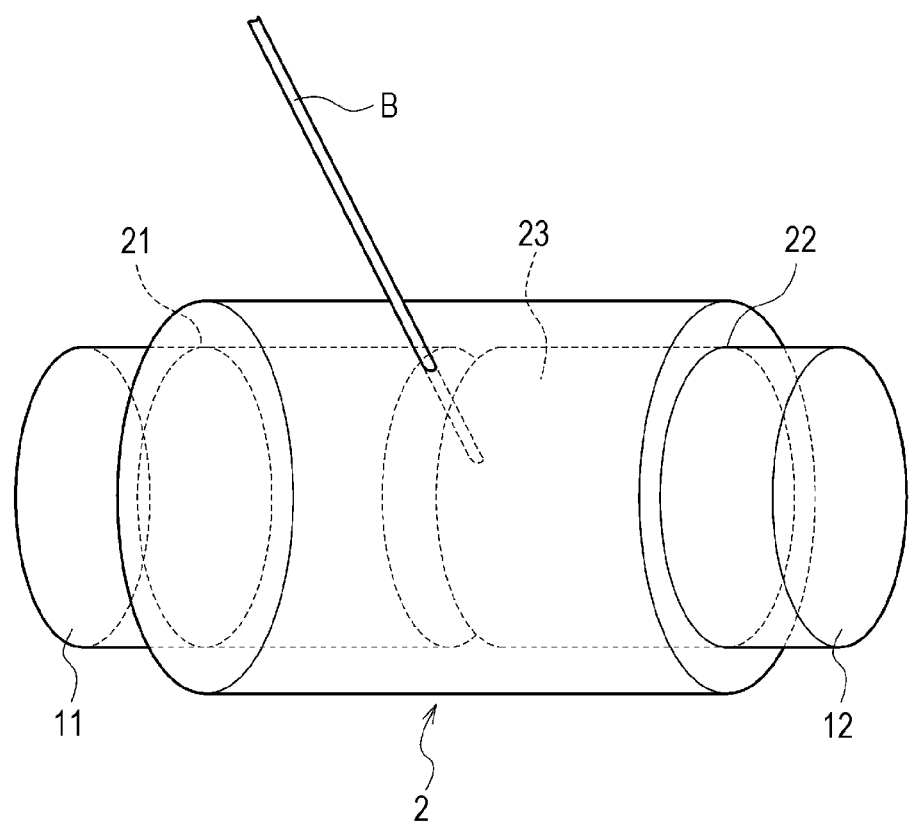
FIG. 2 is a perspective view schematically illustrating the configuration of a sample cartridge related to the present application.
Figure 3:
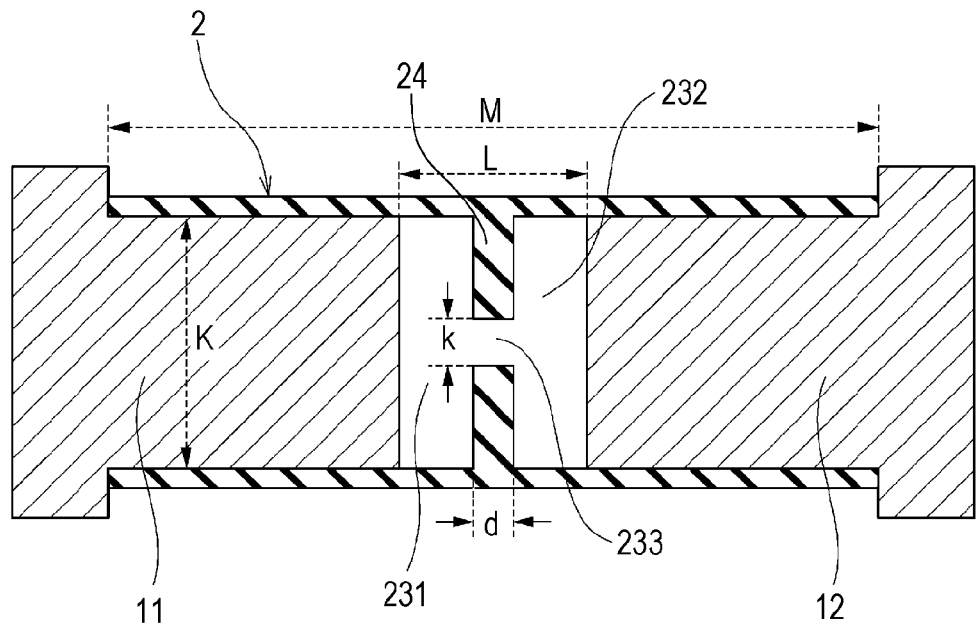
FIG. 3 is a cross-sectional view schematically illustrating the configuration of the sample cartridge related to the present application.

In FIGS. 2 and 3, the configuration of the sample cartridge 2 is schematically illustrated. FIG. 2 is a perspective view and FIG. 3 is a cross-sectional view.

The sample cartridge 2 is made by forming an insulating material into a tubular body. As the insulating material, although it is not particularly limited, for example, a hydrophobic and insulating polymer, copolymer, or blend polymer, such as polypropylene, polymethylmethacrylate, polystyrene, or polytetrafluoroethylene, can be given. Further, the sample cartridge 2 may also be a component in which these hydrophobic and insulating polymers or the like is coated on the surface of a tubular body formed by a given material. The shape of the sample cartridge 2 may also be a tubular body having a polygonal (triangular, quadrangular, or more) cross-section, other than a cylindrical body shown in the drawings.

The above-mentioned electrodes 11 and 12 are inserted into an inner cavity of the tubular body from openings 21 and 22 of both ends of the sample cartridge 2. The above-mentioned electric power supply 3 and the measurement section 41 are connected to the electrodes 11 and 12 through wirings (not shown). The sample cartridge 2 holds the liquid sample in a region 23 which is constituted by the surfaces of the electrodes 11 and 12 and the surface of the inner cavity of the tubular body. For this reason, it is preferable that the region 23 be airtightly configured by hermetically sealing the openings 21 and 22 by the electrodes 11 and 12. However, if stagnation of the liquid sample for a period of time necessary for measurement is possible, the region 23 may not have an airtight configuration. In addition, here, the electrodes 11 and 12 have been described as an external configuration of the sample cartridge 2. However, the electrodes 11 and 12 may also be made as an internal configuration in which they are attached to the sample cartridge 2. In a case where the sample cartridge 2 is made to be disposable, it is preferable that the electrodes 11 and 12 be provided as the external configuration.

Introduction of the liquid sample into the region 23 can be performed by inserting an injection needle B from the outer surface of the cylindrical body into the inner cavity after insertion of the electrodes 11 and 12 into the openings 21 and 22 of both ends of the sample cartridge 2 and then injecting a sample solution. After the injection, a hermetically-sealed state of the region 23 can be maintained by blocking a passing-through portion of the injection needle B by grease or the like. In the case of performing analysis of a blood coagulation system in the measuring device A, blood is introduced into the region 23, an anticoagulant action is released, and measurement is then started.

In the region 23, a narrowing portion 24 which is located between the facing electrodes 11 and 12 and has a narrowed inner cavity is provided (refer to FIG. 3). The narrowing portion 24 is provided by protruding the surface of the inner cavity of the cylindrical body to the inner cavity side. The region 23 is divided into a first region 231 on the electrode 11 side and a second region 232 on the electrode 12 side by the narrowing portion 24 having insulation properties on the basis of an insulating material. Then, a portion of the first region 231 and a portion of the second region 232 are communicated with each other by a narrowing region 233 which is an inner cavity portion of the narrowing portion 24. The liquid sample introduced into the region 23 is continuously filled up in the first region 231, the narrowing region 233, and the second region 232. The narrowing portion 24 may be provided in a plurality. That is, the narrowing regions 233 may be made by perforating a plurality of through-holes in a partition wall provided by protruding the surface of the inner cavity of the cylindrical body to the inner cavity side.

The cross-sectional area of the inner cavity (the narrowing region 233) of the narrowing portion is formed smaller than the area of the surface of each of the electrodes 11 and 12. As will be described in detail below, by this configuration, the complex impedance of the liquid sample filled up in the entirety of the region 23 becomes approximately equal to the complex impedance of the liquid sample present in the narrowing region 233, and the electrical characteristics of the liquid sample present in the narrowing region 233 determine the measurement result of the electrical characteristics of the liquid sample filled up in the entirety of the region 23.

Accordingly, even in a case where a chemical reaction of the liquid sample has progressed in the first region 231 or the second region 232 due to the contact with the electrodes 11 and 12, the electrical characteristics of the liquid sample can be measured without being affected by the chemical reaction. Further, even in a case where interfacial polarization has occurred in the contact surface between the liquid sample and each of the electrodes 11 and 12 in the first region 231 or the second region 232, the electrical characteristics of the liquid sample can be measured without being affected by the interfacial polarization.

Specifically, in the case of performing analysis of a blood coagulation system in the measuring device A, even when an intrinsic coagulation reaction of blood is activated due to the contact with the electrodes 11 and 12 in the first region 231 or the second region 232, so that a coagulation process is accelerated or when interfacial polarization has occurred in the contact surfaces with the electrodes 11 and 12, the permittivity of the blood is measured with a high precision, so that the function of the blood coagulation system can be accurately evaluated.

The cross-section area of the narrowing region 233 is made to be a size of the extent that the complex impedance of the portion of the narrowing region 233 in which the sample solution is filled up becomes sufficiently smaller than the complex impedance of the narrowing portion 24 (a portion except for the narrowing region 233). Further, the upper limit value of the cross-sectional area and the lower limit value of the length (refer to a symbol d in FIG. 3) of the narrowing region 233 are set in accordance with the surface area of each of the electrodes 11 and 12 and the distance (refer to a symbol L in FIG. 3) between the electrodes such that the sum of the complex admittance (the reciprocal of the complex impedance) of the portion of the narrowing region 233 in which the sample solution is filled up and the complex admittance of the narrowing portion 24 (a portion except for the narrowing region 233) becomes approximately equal to the complex admittance of the entirety of the region 23. Further, the cross-section area of the narrowing region 233 is made to be a size of the extent that the electrical characteristics of the sample solution filled up in the narrowing region 233 are not different from the macroscopic electrical characteristics of the sample solution.

In a case where the measurement of the complex impedance of the liquid sample filled up in the region 23 has been performed using the sample cartridge 2, complex impedance $Z_m$ which is observed is expressed by the following expression (1).

$$Z_m = Z_3 + \frac{Z_4 Z_5}{Z_4 + Z_5} + Z_e \qquad \text{expression (1)}$$

(In the expression, $Z_3$ expresses complex impedance by the liquid sample filled up in the first region 231 and the second region 232. $Z_4$ expresses the complex impedance of the narrowing portion 24 (a portion except for the narrowing region 233). $Z_5$ expresses the complex impedance of the liquid sample filled up in the narrowing region 233. $Z_e$ expresses complex impedance by an electrical double layer (interfacial polarization or electrode polarization) which is formed on the surface of each of the electrodes 11 and 12 by positive and negative ions which are included in the sample solution).

First, the expression (1) in a case where $Z_e$ is sufficiently small, being ignorable, is described.

Supposedly, as "Condition 1", in a case where a condition ($Z_3 << Z_4 Z_5/(Z_4+Z_5)$) in which $Z_3$ is sufficiently smaller than $Z_4 Z_5/(Z_4+Z_5)$ is satisfied, $Z_m$ is determined by the second item of the right member of the expression (1).

Further, as "Condition 2", in a case where a condition ($Z_4 >> Z_5$) in which $Z_4$ is sufficiently larger than $Z_5$ is satisfied, the second item of the right member of the expression (1) is expressed by the following expression (2).

$$\frac{Z_4 Z_5}{Z_4 + Z_5} = \frac{Z_5}{1 + Z_5/Z_4} \cong Z_5 \qquad \text{expression (2)}$$

Accordingly, the complex impedance $Z_m$ which is observed becomes equal to the complex impedance $Z_5$ of the liquid sample filled up in the narrowing region 233. This means that in the case of satisfying the above-mentioned "Condition 1" and "Condition 2", the electrical characteristics of the liquid sample present in the narrowing region 233 determine the measurement result of the electrical characteristics of the liquid sample filled up in the entirety of the region 23.

Next, which cases satisfy "Condition 1" and "Condition 2" will be described. The cross-sectional area of each of the electrodes 11 and 12 is set to be S, the distance between the electrodes is set to be L (refer to FIG. 3), the cross-sectional area of the narrowing region 233 is set to be s, the length of the narrowing region 233 is set to be d (refer to FIG. 3), the complex permittivity of the liquid sample is set to be $\in_s$, and the complex permittivity of an insulating material constituting the narrowing portion 24 is set to be $\in_i$.

The following expression (3) is derived by "Condition 2".

$$s\in_s >> (S-s)\in_i \qquad \text{expression (3)}$$

Further, the following expression (4) is derived by "Condition 1".

$$S\in_s/(L-d) >> s\in_s/d + (S-s)\in_i/d \qquad \text{expression (4)}$$

The complex permittivity $\in_s$ of the liquid sample is much larger than the complex permittivity $\in_i$ of the insulating material constituting the narrowing portion 24 over a wide frequency range. For example, in the case of using blood as the liquid sample, the complex permittivity $\in_s$ of the blood is much larger than the complex permittivity $\in_i$ of an insulating plastic such as polypropylene in a wide frequency range of 1 Hz to 10 GHz. Accordingly, for example, by setting the dimension of each portion of the sample cartridge 2 to be a value as shown in, for example, FIG. 4, it is possible to satisfy the above-mentioned Expressions (3) and (4). In addition, in FIG. 4, for the sake of convenience, only the electrode on one side is illustrated.

As for the dimension of each portion of the sample cartridge 2, it is preferable that the diameter k of the narrowing region 233 be in a range of 0.02 mm to 10 mm, the length d of the narrowing region 233 be in a range of 0.02 mm to 90 mm, the diameter K of each of the electrodes 11 and 12 be in a range of 0.2 mm to 100 mm, and the distance L between the electrodes 11 and 12 be 0.22 mm to 290 mm. The diameter k and the length d of the narrowing region 233 are set to be sufficiently large to the extent that the electrical characteristics of the sample solution filled up in the narrowing region 233 can represent the macroscopic electrical characteristics of the sample solution. Further, the distance L between the electrodes 11 and 12 (or the distance from each electrode to the narrowing portion 24) is set to be sufficiently large to the extent that it is possible to prevent the influence of a chemical reaction or interfacial polarization occurred in the electrode surface on the liquid sample present in the narrowing region 233.

Subsequently, in a case where $Z_e$ is not negligible, Expression (1) which includes the complex impedance $Z_e$ due to interfacial polarization will be described.

Positive and negative ions which are included in the sample solution are accumulated in the vicinity of the electrode, thereby forming an electrical double layer, whereby electrode polarization is generated, and the lower the frequency measurement, the more the influence thereof becomes prominent. If the frequency of a dielectric response of a sample to be observed is higher than a frequency at which electrode polarization becomes prominent, the influence of electrode polarization does not matter.

Here, since the narrowing portion 24 made of an insulating material is present in the sample cartridge 2, an ion current passes through the inner cavity (the narrowing region 233) of the portion of the narrowing portion 24. The ion current passing through the narrowing region 233 drastically becomes small compared to an ion current in the case of a general capacitor type electrode cell having no narrowing portion 24. For this reason, it also becomes difficult for accumulation of ions in the vicinity of the electrodes 11 and 12 to occur. Accordingly, in the sample cartridge 2, a frequency at which electrode polarization becomes prominent shifts to the low-frequency side compared to the general capacitor type electrode cell. That is, it becomes difficult to be affected by electrode polarization.

EXAMPLE

The dielectric spectroscopic measurement of a blood coagulation process was carried out using the sample cartridge related to the present application. As for the sample cartridge, the blood, and the measuring device, the following were used.

(1) Sample Cartridge

Figure 4:
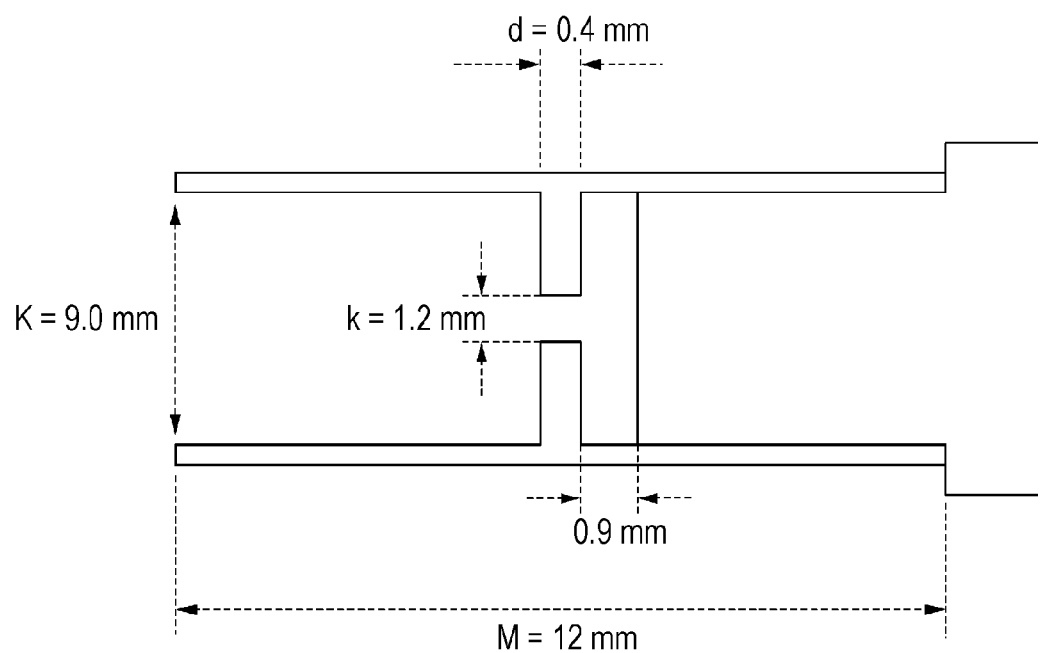
FIG. 4 is a schematic diagram illustrating the dimension of each portion of the sample cartridge used in an example.

A sample cartridge having the shape shown in FIG. 4 was manufactured using polypropylene. As the electrode, an electrode in which gold plating is applied to copper was used. Further, for comparison, a general capacitor type electrode cell having no narrowing portion was also used. In addition, in FIG. 4, for the sake of convenience, only the electrode on one side is illustrated.

(2) Blood

An erythrocyte suspension was prepared by purchasing rabbit preserved blood from Kohjin Bio Co., Ltd. and washing it with PBS. Bovine-derived fibrinogen was purchased from Sigma Corp., dissolved in PBS, and adjusted such that the fibrinogen concentration was 0.5 wt %. Bovine-derived thrombin was purchased from Sigma Corp. and adjusted so as to become 0.01% (about 10 units/ml). A coagulation reaction was started by adjusting model blood having a hematocrit of about 25% and a fibrinogen concentration of 0.25% by mixing the erythrocyte suspension and the fibrinogen solution, and adding 5 μl (50 munits/ml) of the thrombin solution per 1 ml of the model blood just before the dielectric spectroscopic measurement. Further, for comparison, the measurement of a negative control without addition of thrombin was also performed. In the measurement with thrombin added, an added time was set to be time 0.

(3) Measuring Device

Dielectric measurement was performed using an impedance analyzer (4294A) made by Agilent Technologies Japan Ltd. and with the conditions of a measuring frequency range of 40 Hz to 110 MHz, a measurement time interval of 1 minute, and measurement temperature of 37° C. Further, a coagulation starting time was sought by measuring the same model blood as the above by a free oscillation type rheometer and observing a change in viscoelasticity and compared with the measurement result by dielectric spectroscopy.

Figure 5:
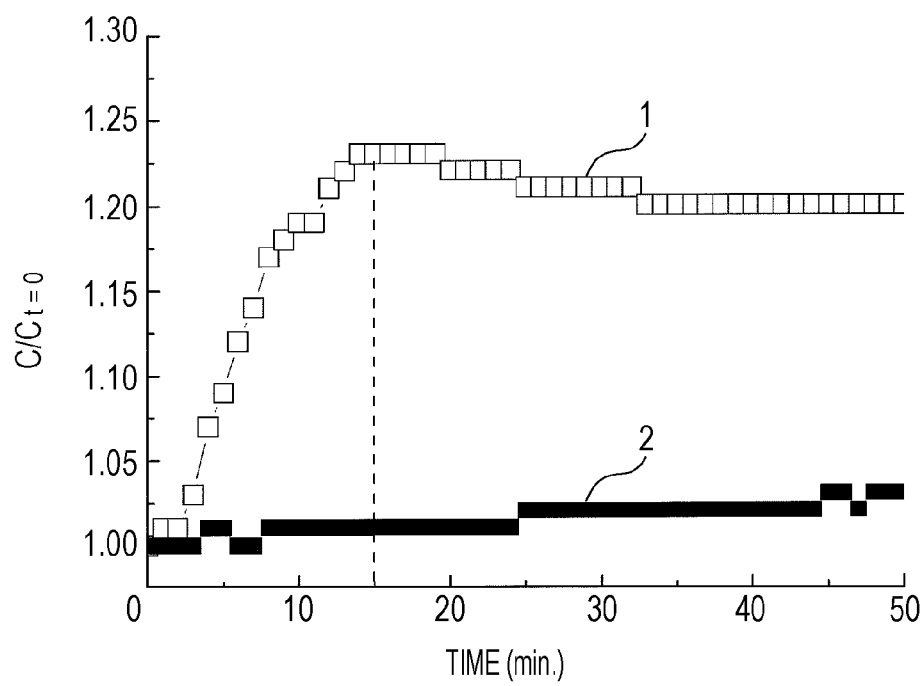
FIG. 5 is a graph showing the results of the dielectric spectroscopic measurement of a blood coagulation process in the example.

The measurement results by dielectric spectroscopy are shown in FIG. 5. The drawing shows a temporal change in capacitance value in 840 kHz. The capacitance value was represented by a value normalized by being divided by a capacitance value in time zero. A symbol 1 indicates the results measured adding the thrombin solution to the model blood, and a symbol 2 indicates the results measured without adding the thrombin solution.

In the model blood with the thrombin solution added thereto, the capacitance value increased with the progress of a coagulation process and showed the maximum value at a time of 15 minutes. On the other hand, in the negative control without addition of the thrombin solution, the capacitance value almost did not change. From this, it was found that a change in electrical characteristics associated with a blood coagulation process could be effectively measured using the sample cartridge related to the present application.

Figure 6:
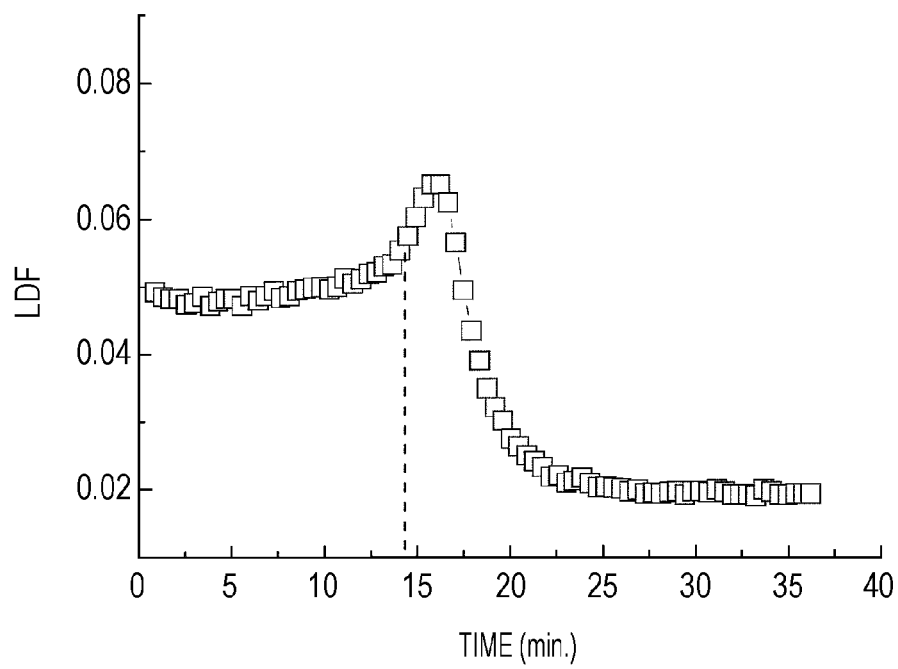
FIG. 6 is a graph showing the measurement results of a blood coagulation process measured by using a free oscillation type rheometer in the example.

The measurement results by the free oscillation type rheometer are shown in FIG. 6. A logarithmic damping factor (LDF) changes from a time of about 14 minutes in accordance with the progress of a coagulation process and it was found that the time is a coagulation starting time. Here, it was found that the coagulation starting time approximately corresponds with a time when the capacitance value shows the maximum value in FIG. 5. From this, it was found that the coagulation starting time of blood could be obtained by the dielectric spectroscopic measurement using the cartridge related to the present application.

Figure 7:
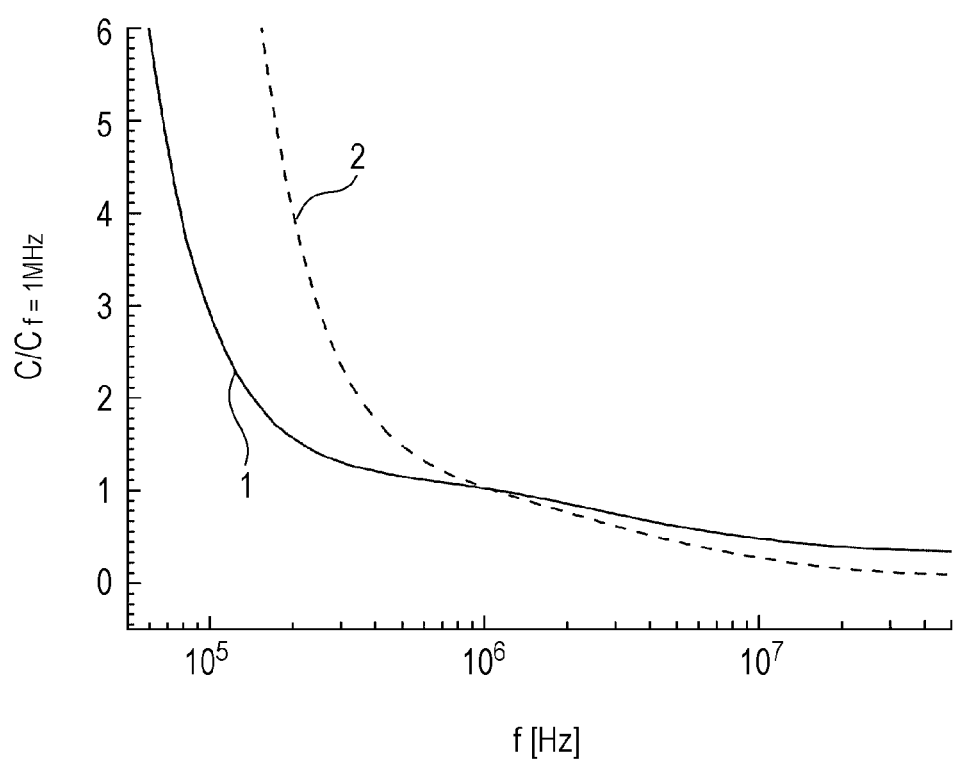
FIG. 7 is a graph showing the results of the dielectric spectroscopic measurement of a blood coagulation process carried out by using the sample cartridge related to the present application and a capacitor type electrode cell used in the past in the example.

The results of dielectric spectroscopic measurements carried out using the sample cartridge related to the present application and the capacitor type electrode cell used in the past are shown in FIG. 7. A symbol 1 indicates the result of the measurement carried out using the sample cartridge related to the present application and a symbol 2 indicates the result of the measurement carried out using the capacitor type electrode cell. The capacitance value was represented by a value normalized by being divided by a capacitance value at 1 MHz.

It was found that in either result, the capacitance value prominently increases along with a decrease in frequency in the low-frequency side. This change is due to electrode polarization. Here, it was found that when using the sample cartridge related to the present application, a frequency, at which electrode polarization becomes prominent, further shifts to a low frequency. This shows that when using the sample cartridge related to the present application, it is difficult for there to be an effect due to the electrode polarization.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A sample cartridge for measuring the electrical characteristics of a liquid sample, the sample cartridge being made by forming an insulating material into a tubular body having a first end and a second end,
    wherein the sample cartridge is configured to hold the liquid sample in a region that is defined by: (1) outer surfaces of two electrodes that face each other and are respectively inserted within an inner cavity of the tubular body between the first and second ends and (2) a first surface and a second surface of the inner cavity that face each other, and
    wherein a narrowing portion comprising a narrowed inner cavity is provided between the outer surfaces of the two electrodes, wherein the narrowing portion is formed by (1) a first partition wall that protrudes to the inner cavity side from at least a first portion of the first surface of the inner cavity of the tubular body and (2) a second partition wall that protrudes to the inner cavity side from at least a second portion of the second surface of the inner cavity of the tubular body,
    wherein the first partition wall and the second partition wall are formed opposite to each other and face each other,
    wherein the first surface of the inner cavity and the second surface of the inner cavity are formed between the outer surfaces of the two electrodes facing each other.

2. The sample cartridge according to claim 1, wherein a cross-sectional area of the narrowed inner cavity of the narrowing portion is smaller than an area of each of the outer surfaces of the two electrodes facing each other.

3. The sample cartridge according claim 1, wherein the narrowing portion is in contact with the outer surfaces of the two electrodes facing each other.

4. The sample cartridge according claim 1, wherein the insulating material comprises a hydrophobic polymer, copolymer or blend polymer containing a polymer selected from the group consisting of: polypropylene, polymethylmethacrylate, polystyrene and polytetrafluoroethylene.

5. The sample cartridge according claim 1, wherein the narrowing portion is formed of the insulating material used to form the tubular body.

6. A sample cartridge for measuring the electrical characteristics of a liquid sample, comprising:
    a tubular body formed of an insulating material and having a first end and a second end; and
    two electrodes which face each other and are respectively inserted within an inner cavity of the tubular body between the first and second ends,
    wherein the sample cartridge is configured to hold the liquid sample in a region that is defined by outer surfaces of the two electrodes facing each other and a first surface and a second surface of the inner cavity of the tubular body that face each other, and
    wherein a narrowing portion comprising a narrowed inner cavity is provided between the outer surfaces of the two electrodes, wherein the narrowing portion is formed by (1) a first partition wall that protrudes to the inner cavity side from at least a first portion of the first surface of the inner cavity of the tubular body and (2) a second partition wall that protrudes to the inner cavity side from at least a second portion of the second surface of the inner cavity of the tubular body, wherein the first partition wall and the second partition wall are formed opposite to each other and face each other, wherein the first surface of the inner cavity and the second surface of the inner cavity are formed between the outer surfaces of the two electrodes facing each other.

7. A device for measuring the electrical characteristics of a liquid sample, comprising:

a pair of electrodes configured to apply voltage to the liquid sample;

a sample cartridge which is made by forming an insulating material into a tubular body having a first end and a second end and is configured to hold the liquid sample in a region that is defined by: (1) outer surfaces of the electrodes that face each other and are respectively inserted within an inner cavity of the tubular body between the first and second ends, and (2) a first surface and a second surface of the inner cavity that face each other, and wherein a narrowing portion comprising a narrowed inner cavity is provided between the outer surfaces of the pair of electrodes, wherein the narrowing portion is formed by (1) a first partition wall that protrudes to the inner cavity side from at least a first portion of the first surface of the inner cavity of the tubular body and (2) a second partition wall that protrudes to the inner cavity side from at least a second portion of the second surface of the inner cavity of the tubular body, wherein the first partition wall and the second partition wall are formed opposite to each other and face each other, wherein the first surface of the inner cavity and the second surface of the inner cavity are formed between the outer surfaces of the pair of electrodes facing each other;

an applying section configured to apply voltage to the pair of electrodes; and a measuring section configured to measure the electrical characteristics of the liquid sample.

8. The device according to claim 7, wherein the measuring section is configured to measure the electrical characteristics of the liquid sample present in the narrowed inner cavity.

9. A blood coagulation system analysis device comprising:

a pair of electrodes configured to apply voltage to blood;

a sample cartridge which is made by forming an insulating material into a tubular body having a first end and a second end and is configured to hold the blood in a region that is defined by: (1) outer surfaces of the pair of electrodes that face each other and are inserted within an inner cavity of the tubular body between the first and second ends, and (2) a first surface and a second surface of the inner cavity that face each other, and wherein a narrowing portion comprising a narrowed inner cavity is provided between the outer surfaces of the pair of electrodes, wherein the narrowing portion is formed by (1) a first partition wall that protrudes to the inner cavity side from at least a first portion of the first surface of the inner cavity of the tubular body and (2) a second partition wall that protrudes to the inner cavity side from at least a second portion of the second surface of the inner cavity of the tubular body, wherein the first partition wall and the second partition wall are formed opposite to each other and face each other, wherein the first surface of the inner cavity and the second surface of the inner cavity are formed between the outer surfaces of the pair of electrodes facing each other;

an applying section configured to apply alternating-current voltage to the pair of electrodes; and a measuring section configured to measure the permittivity of the blood.

10. The blood coagulation system analysis device according to claim 9, wherein the measuring section is configured to measure the permittivity of the blood present in the narrowed inner cavity.

* * * * *